(12) United States Patent
Stewart et al.

(10) Patent No.: US 11,298,447 B2
(45) Date of Patent: Apr. 12, 2022

(54) GASLESS EXTRA-CORPOREAL CARBON DIOXIDE REMOVAL

(71) Applicant: Government of the United States as represented by the Secretary of the Air Force, Wright-Patterson AFB, OH (US)

(72) Inventors: Ian J. Stewart, Lodi, CA (US); Jeremy W. Cannon, Philadelphia, PA (US)

(73) Assignee: United States of America as represented by the Secretary of the Air Force, Wright-Patterson AFB, OH (US)

(*) Notice: Subject to any disclaimer, the term of this patent is extended or adjusted under 35 U.S.C. 154(b) by 594 days.

(21) Appl. No.: 16/266,193

(22) Filed: Feb. 4, 2019

(65) Prior Publication Data

US 2020/0246530 A1   Aug. 6, 2020

(51) Int. Cl.
*A61M 1/34* (2006.01)
*B01D 69/08* (2006.01)
(Continued)

(52) U.S. Cl.
CPC ........ *A61M 1/3486* (2014.02); *A61M 1/3479* (2014.02); *A61M 1/3627* (2013.01); *B01D 69/08* (2013.01); *B01D 71/16* (2013.01); *B01D 71/38* (2013.01); *B01D 71/42* (2013.01); *B01D 71/68* (2013.01); *A61M 2202/0225* (2013.01);
(Continued)

(58) Field of Classification Search
CPC .............. A61M 1/3486; A61M 1/3479; A61M 1/3627; A61M 1/3679; A61M 2202/0225; A61M 2205/3337; A61M 2205/3334; B01D 61/246; B01D 63/02; B01D 69/08; B01D 69/081; B01D 71/16; B01D 71/38; B01D 71/42; B01D 71/56; B01D 71/68; B01D 2311/2626; B01D 2313/40; B01D 2313/44; B01D 2315/12; B01D 2325/20
See application file for complete search history.

(56) References Cited

U.S. PATENT DOCUMENTS 4,602,987 A * 7/1986 Bonaventura ........... H01M 8/06
                                                           205/633
5,850,833 A * 12/1998 Kotliar .................... A61G 10/04
                                                           128/202.12
(Continued)

OTHER PUBLICATIONS

P. Morimont et al., "Update on the role of extracorporeal CO2 removal as an adjunct to mechanical ventilzation in ARDS," Critical Care, vol. 19:117 (2015) 7 pages total.
(Continued)

*Primary Examiner* — John Kim
(74) *Attorney, Agent, or Firm* — AFMCLO/JAZ; Charity D. S. Whitaker

(57) ABSTRACT

A carbon dioxide absorption medium. The absorption medium includes a plurality of hollow fibers and a plurality of binder particles. The hollow fibers have walls comprising a selectively permeable membrane that is configured to permit passage of gaseous carbon dioxide but not liquids. The plurality bind particles are dispersed between the hollow fibers and comprise an absorbent material configured to absorb gaseous carbon dioxide and to bind the carbon dioxide in a solid state.

23 Claims, 3 Drawing Sheets

(51) Int. Cl.
  *B01D 71/16* (2006.01)
  *B01D 71/68* (2006.01)
  *B01D 71/42* (2006.01)
  *B01D 71/38* (2006.01)
  *A61M 1/36* (2006.01)
  *B01D 61/24* (2006.01)
  *B01D 71/56* (2006.01)

(52) U.S. Cl.
  CPC ............... *A61M 2205/3334* (2013.01); *A61M 2205/3337* (2013.01); *B01D 61/246* (2013.01); *B01D 71/56* (2013.01); *B01D 2313/44* (2013.01); *B01D 2325/20* (2013.01)

(56) References Cited

U.S. PATENT DOCUMENTS

| | | | | |
|---|---|---|---|---|
| 8,973,580 | B1* | 3/2015 | Williams | A61M 16/208 128/205.28 |
| 9,199,016 | B2 | 12/2015 | Yoshida et al. | |
| 2003/0074062 | A1 | 4/2003 | Monzyk et al. | |
| 2012/0226258 | A1* | 9/2012 | Otto | A61M 1/3489 604/500 |
| 2013/0333561 | A1 | 12/2013 | Yoshida et al. | |
| 2017/0072339 | A1 | 3/2017 | Yoshida et al. | |

OTHER PUBLICATIONS

Baxter Healthcare Corp., "The Prismaflex System" Brochure available at https://www.baxter.com/sites/g/files/ebysai746/files/2017-11/Prismaflex-07.11-Brochure-New_Accts.pdf (2017) 12 pages total.
Alung Technologies Inc., Hemolung RAS Brochure, Brochure available at http://pdf.medicalexpo.com/pdf/alung-technologies/hemolung-ras-brochure/81440-105435.html (2012) 2 pages total.
Medica S.P.A., "DECAPsmart Plus," Brochure available at https://www.medica.it/PDF/DecapSmartPlus_eng.pdf (2014) 2 pages total.
Inspiration Healthcare, "Adulta Intensive Care (ICU) Novalung ILA Activve," Information available at https://www.inspiration-healthcare.com/products/adult-intensive-care-icu/novalung-ila-activve (2019) 2 pages total.

* cited by examiner

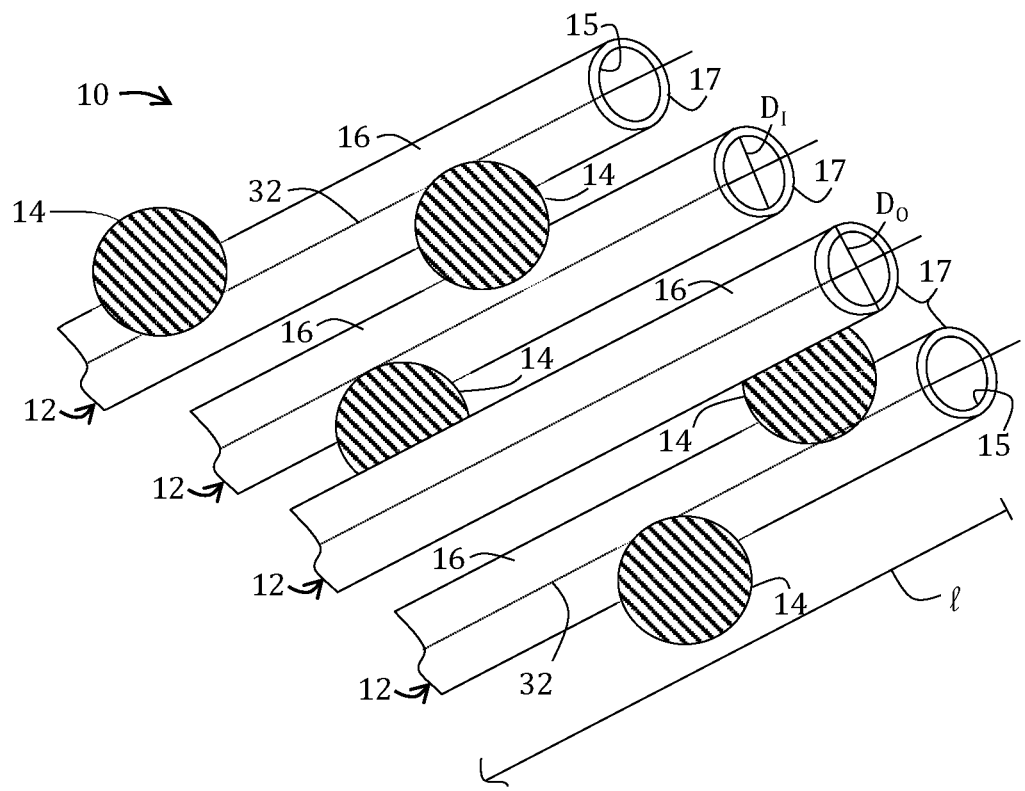
FIG. 1
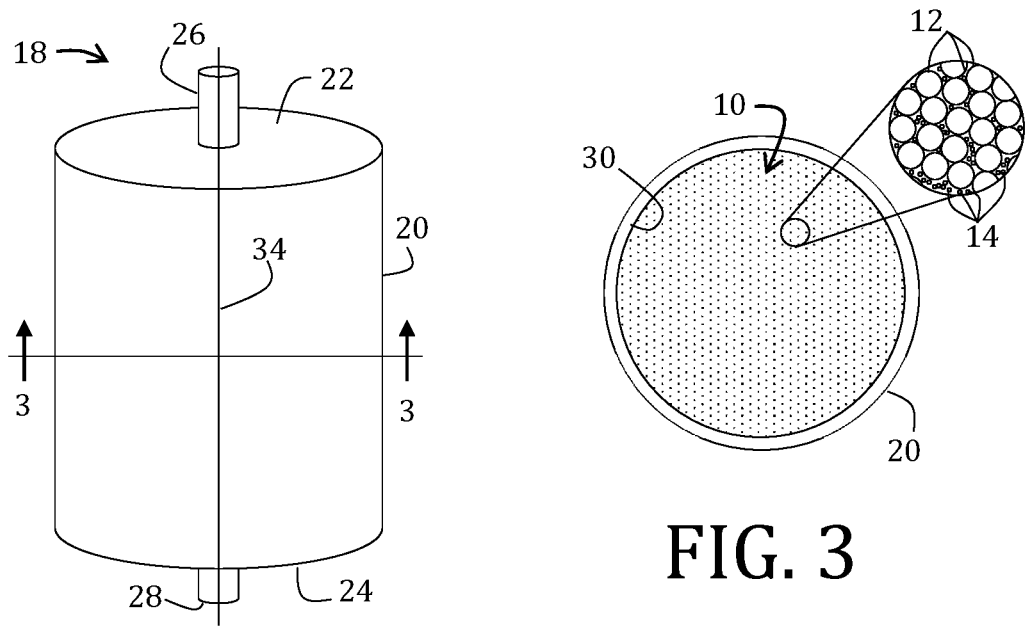
FIG. 2
FIG. 3

GASLESS EXTRA-CORPOREAL CARBON DIOXIDE REMOVAL

GOVERNMENT INTEREST

The invention described herein may be manufactured and used by or for the Government of the United States for all governmental purposes without the payment of any royalty.

FIELD OF THE INVENTION

The present invention relates generally to respiratory disorder treatments and, more specifically, to the treatment of elevated carbon dioxide levels in the blood due to respiratory disorders.

BACKGROUND OF THE INVENTION

Under normal functioning, the lungs of humans and other mammals inspire oxygen gas ($O_2$) from the air and transfer this oxygen to the hemoglobin of blood for transport throughout the body. Carbon dioxide gas ($CO_2$) is collected from throughout the body and transported via the blood to the lungs where it is extracted from the hemoglobin and removed from the body.

Medical patients experiencing significant impairment of the respiratory functioning of the lungs may suffer from elevated carbon dioxide levels in the blood, a condition known as hypercapnia. Conventional medical treatments for patients suffering from hypercapnia have involved taking blood out of the body and circulating the blood along a first side of a membrane while a carrier (i.e., sweep) gas flows along a second side of the membrane. Carbon dioxide gas diffuses across the membrane and is carried or swept away by the carrier gas. In this manner, the carbon dioxide level of the blood may be extra-corporeally reduced.

Extra-corporeal carbon dioxide removal systems of this type, however, are bulky and cumbersome. Much of this is due to the need for a continuous supply of the carrier gas during the procedure. Large, high pressure gas cylinders, along with associated pressure regulation and other safety equipment, are necessary to provide the flow of carrier gas. Such conventional systems end up being impractical in austere treatment environments and/or in treatment environments with limited physical space, such as in aeromedical evacuations.

Thus, there is a continuing need for blood carbon dioxide removal technologies and, particularly, to carbon dioxide removal systems that may be used in a non-traditional medical treatment setting.

SUMMARY OF THE INVENTION

The present invention overcomes the foregoing problems and other shortcomings, drawbacks, and challenges of conventional carbon dioxide removal systems. While the invention will be described in connection with certain embodiments, it will be understood that the invention is not limited to these embodiments. To the contrary, this invention includes all alternatives, modifications, and equivalents as may be included within the spirit and scope of the present invention In response to these issues, the present invention provides, in a first aspect, a carbon dioxide absorption media. In accordance with one aspect, this carbon dioxide absorption medium includes a plurality of hollow fibers and a plurality of binder particles. The hollow fibers have a proximal end, a distal end, a lumen between the proximal and distal ends, and a wall surrounding the lumen. The walls of the hollow fibers comprise a membrane selectively permeable to gaseous carbon dioxide. The binder particles are dispersed between the plurality of hollow fibers and are configured to absorb gaseous carbon dioxide and bind the carbon dioxide in a solid state.

In certain embodiments of the absorption medium the membrane comprising the walls of the hollow fibers is formed from at least one polymer selected from the group consisting of cellulose acetate, cellulose triacetate, polyamide, polysulfone, polyethersulfone ("PES"), polyacrylonitrile ("PAN"), sulfonated polyacrylonitrile, polymethylmethacrylate ("PmmA"), and polymethylpentene ("PMP").

In certain embodiments of the absorption medium the walls have a thickness ranging from about 5 µm to about 50 µm.

In certain embodiments of the absorption medium the binder particles have a maximum dimension ranging from about 100 µm to about 10,000 µm.

In certain embodiments of the absorption media, the binder particles are made up of at least one absorbent material selected from the group consisting of sodium oxide, sodium hydroxide, calcium oxide, calcium hydroxide, potassium hydroxide, lithium hydroxide, lithium peroxide, lithium carbonate, and lithium chloride.

In a second aspect, a carbon dioxide absorption cartridge for extra-corporeal absorption of carbon dioxide from the blood of a patient is provided. The cartridge includes an extra-corporeal housing having an inlet port, an outlet port, and an internal cavity therebetween. A carbon dioxide absorption medium is disposed within the internal cavity of the housing. The carbon dioxide absorption medium includes a plurality of hollow fibers and a plurality of binder particles. The hollow fibers have a proximal end, a distal end, a lumen between the proximal and distal ends, and a wall surrounding the lumen. The walls of the hollow fibers comprise a membrane selectively permeable to gaseous carbon dioxide. The binder particles are dispersed between the plurality of hollow fibers and are configured to absorb gaseous carbon dioxide and bind the carbon dioxide in a solid state.

In certain embodiments of the cartridge the membrane comprising the walls of the hollow fibers is formed from at least one polymer selected from the group consisting of cellulose acetate, cellulose triacetate, polyamide, polysulfone, polyethersulfone ("PES"), polyacrylonitrile ("PAN"), sulfonated polyacrylonitrile, polymethylmethacrylate ("PmmA"), and polymethylpentene ("PMP").

In certain embodiments of the cartridge the walls have a thickness ranging from about 5 µm to about 50 µm.

In certain embodiments of the cartridge the binder particles have a maximum dimension ranging from about 100 µm to about 10,000 µm.

In certain embodiments of the cartridge the binder particles are made up of at least one absorbent material selected from the group consisting of sodium oxide, sodium hydroxide, calcium oxide, calcium hydroxide, potassium hydroxide, lithium hydroxide, lithium peroxide, lithium carbonate, and lithium chloride.

In certain embodiment of the cartridge the internal cavity comprising a first partition and a second partition that is fluidically isolated from the first partition. The proximal ends of the hollow fibers of the plurality extend into the first partition while the distal ends of the hollow fibers of the plurality and the plurality of binder particles reside within the second partition. The flow of blood through the housing is thus restricted to flow through the plurality of hollow fibers.

In a third aspect, a blood treatment system is provided. The system includes a carbon dioxide absorption cartridge, a first blood flow path, and a second blood flow path. The first blood flow pathway extends between a patient and the inlet port of the housing of the carbon dioxide absorption cartridge. The second blood flow pathway extends between the outlet port of the housing of the carbon dioxide absorption cartridge and the patient. The cartridge includes an extra-corporeal housing having an inlet port, an outlet port, and an internal cavity therebetween. A carbon dioxide absorption medium is disposed within the internal cavity of the housing. The carbon dioxide absorption medium includes a plurality of hollow fibers and a plurality of binder particles. The hollow fibers have a proximal end, a distal end, a lumen between the proximal and distal ends, and a wall surrounding the lumen. The walls of the hollow fibers comprise a membrane selectively permeable to gaseous carbon dioxide. The binder particles are dispersed between the plurality of hollow fibers and are configured to absorb gaseous carbon dioxide and bind the carbon dioxide in a solid state.

The system also includes a first extra-corporeal blood flow pathway for transporting blood—which has an elevated amount of carbon dioxide—from a first vein of the patient to the housing inlet port, as well as a pump for pumping blood through the first extra-corporeal blood flow pathway. In addition, the system includes a second extra-corporeal blood flow pathway for transporting blood—now having a reduced amount of carbon dioxide—from the housing outlet port to a second vein of the patient.

According to the system embodiment blood flows from the housing inlet port to the outlet port through the interior volumes of the plurality of hollow fibers. As the blood flows through the hollow fibers, gaseous carbon dioxide from the blood passes across the semi-permeable membranes of the fibers and is absorbed by the binder particles so that the amount of carbon dioxide in the blood is reduced.

In certain embodiments of the system the first extra-corporeal blood flow pathway comprises a first length of tubing in flow communication with a first catheter lumen which is inserted into the first vein of the patient, and the second extra-corporeal blood flow pathway comprises a second length of tubing in flow communication with a second catheter lumen which is inserted into the second vein of the patient In certain embodiments of the system the first and second veins are the same vein of the patient and the first and second lumens are both part of a multi-lumen catheter.

In certain embodiments of the system, the pump is a peristaltic pump.

In certain embodiments of the system the semi-permeable membrane is formed from at least one polymer selected from the group consisting of cellulose acetate, cellulose triacetate, polyamide, PES, PAN, sulfonated polyacrylonitrile, PmmA, and PMP.

In certain embodiments of the system, the semi-permeable membrane has an average thickness from about 5 µm to about 50 µm.

In certain embodiments of the system the binder particles have an average particle diameter from about 100 µm to about 10,000 µm.

In certain embodiments of the system the binder particles are made up of at least one absorbent material selected from the group consisting of sodium oxide, sodium hydroxide, calcium oxide, calcium hydroxide, potassium hydroxide, lithium hydroxide, lithium peroxide, lithium carbonate, and lithium chloride.

In certain embodiments of the system, the absorption media removes from about 50 mL/min to about 100 mL/min of carbon dioxide from the blood, as measured at about atmospheric pressure and at a temperature from about 35° C. to about 39° C.

In certain embodiments of the system, the blood flows through the absorption media at a rate from about 0.2 L/min to about 0.5 L/min.

In certain embodiments of the system, no carrier gas flows through the absorption media.

In certain embodiments of the system, the system also includes a dialyzer along the first blood flow pathway or the second blood flow pathway and is configured to perform hemodialysis.

In a fourth aspect, a method for removing carbon dioxide from blood is provided. According to one embodiment, the method includes transporting blood from a patient to a carbon dioxide absorption cartridge. The cartridge includes an extra-corporeal housing having an inlet port, an outlet port, and an internal cavity therebetween. A carbon dioxide absorption medium is disposed within the internal cavity of the housing. The carbon dioxide absorption medium includes a plurality of hollow fibers and a plurality of binder particles. The hollow fibers have a proximal end, a distal end, a lumen between the proximal and distal ends, and a wall surrounding the lumen. The walls of the hollow fibers comprise a membrane selectively permeable to gaseous carbon dioxide. The binder particles are dispersed between the plurality of hollow fibers and are configured to absorb gaseous carbon dioxide and bind the carbon dioxide in a solid state. The blood is moved through the carbon dioxide absorption cartridge, thereby removing carbon dioxide from the blood. The blood is then transported from the carbon dioxide absorption cartridge to the patient.

According to the method, the blood is further pumped from the housing inlet port to the outlet port through the interior volumes of the plurality of hollow fibers. As the blood flows through the hollow fibers, gaseous carbon dioxide from the blood passes across the semi-permeable membranes of the fibers and is absorbed by the binder particles so that the amount of carbon dioxide in the blood is reduced.

The method also includes returning the blood having a reduced amount of carbon dioxide from the housing outlet port to a second vein of the patient through a second extra-corporeal blood flow pathway.

In certain embodiments of the method, the membrane comprising the walls of the hollow fibers is formed from at least one polymer selected from the group consisting of cellulose acetate, cellulose triacetate, polyamide, polysulfone, PES, PAN, sulfonated polyacrylonitrile, PmmA, and PMP.

In certain embodiments of the method, the walls have a thickness ranging from about 5 µm to about 50 µm.

In certain embodiments of the method, the binder particles have a maximum dimension ranging from about 100 µm to about 10,000 µm.

In certain embodiments of the method, the binder particles are made up of at least one absorbent material selected from the group consisting of sodium oxide, sodium hydroxide, calcium oxide, calcium hydroxide, potassium hydroxide, lithium hydroxide, lithium peroxide, lithium carbonate, and lithium chloride.

In certain embodiments of the method, carbon dioxide is removed from the blood at a rate ranging from about 50 mL/min to about 100 mL/min.

In certain embodiments of the method, blood flows at a rate ranging from about 0.2 L/min to about 0.5 L/min.

In certain embodiments of the method, no carrier gas flows through the absorption media.

In certain embodiments of the method, the method also includes performing hemodialysis on the blood using a dialyzer to remove excess urea from the blood.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

Other embodiments of the invention will become apparent by reference to the detailed description in conjunction with the figures, wherein elements are not to scale so as to more clearly show the details, wherein like reference numbers indicate like elements throughout the several views, and wherein:

FIG. 1 is a side elevational, schematic view of a carbon dioxide absorption media according to an embodiment of the present invention.

FIG. 2 is a perspective view of a carbon dioxide absorption cartridge according to an embodiment of the present invention.

FIG. 3 is cross-sectional view through the carbon dioxide absorption cartridge of FIG. 2 along the line 3-3.

Figure 4:
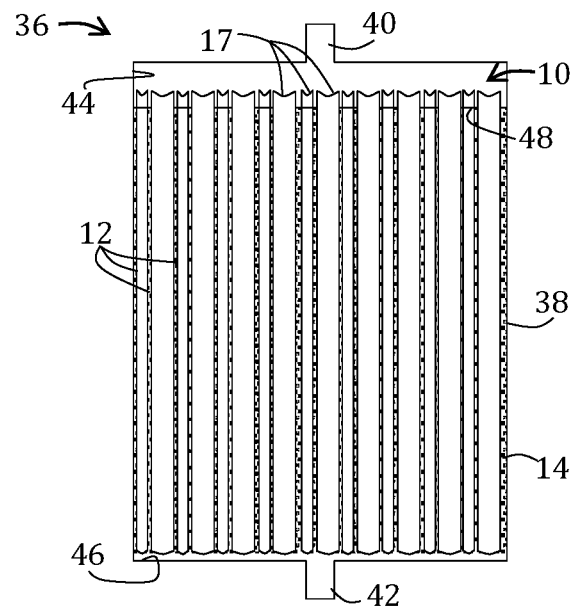
FIG. 4 is a cross-sectional view of carbon dioxide absorption cartridge according to another embodiment of the present invention.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION OF THE INVENTION

Referring now to the figures, and in particular to FIG. 1, an absorption media 10 according to a first embodiment is described and includes a plurality of hollow fibers 12 with binder particles 14 distributed among, as opposed to within, the hollow fibers 12. Each hollow fiber 12 may have a length (l), an outer diameter ($D_o$), and an interior diameter ($D_I$) defining a lumen 15 that extends the length of the fiber 12.

While the length of the hollow fibers 12 may vary somewhat in accordance with a desired embodiment, lengths of the hollow fibers 12 may range from about 20 cm to about 24 cm. Typical $D_o$ of the hollow fibers 12 vary also by embodiment and may depend, at least in part, on a thickness of fiber walls 16, desired maximum $D_o$, and a desired maximum $D_I$, the latter of which correlating to a desired flow rate. Generally, $D_o$ may range from about 200 µm to about 250 µm.

Walls 16 of the hollow fibers 12 may be formed from a semi-permeable membrane material configured to permit passage of at least gaseous carbon dioxide, but limits or resists passage of liquids, across the membrane. Suitable materials for the wall 16 may include, but are not limited to, cellulose acetate, cellulose triacetate, polyamide, polysulfone, polyethersulfone ("PES"), polyacrylonitrile ("PAN"), sulfonated polyacrylonitrile, polymethylmethacrylate ("PmmA"), and polymethylpentene ("PMP"). According to some embodiments, the walls 16 may comprise a blend of one or more of these materials, with or without additives, such as those that inhibit clotting of blood as to moves through the fibers 12, antimicrobial materials, or other materials that increase the strength and/or durability of the fibers 12. In that regard and according to some embodiments, an entire length of the walls 16 of the hollow fibers 12 may be comprised of one material (or composite of materials) while other embodiments permit variation of materials comprising the walls 16 along the length of the hollow fiber 12. For example, the wall 16 of a proximal end 17, a distal end (not shown), or both of the hollow fiber 12 may be constructed from one material while a medial section may be constructed from a second material, such as one having a greater porosity or permeability as compared to the first material. Such embodiments may facilitate the incorporation of the hollow fibers 12 into a system, as described in greater detail below.

While the thickness of the wall 16 used to form the hollow fibers 12 may vary somewhat, thickness may range from about 5 µm to about 50 µm.

Referring still to FIG. 1, the binder particles 14 may be small bead-like particulates, as shown, that are loosely packed between the hollow fibers 12. These binder particles 14 are configured to absorb gaseous carbon dioxide and bind the same in a solid state without the need for a carrier gas; although, a carrier gas may be used, if desired, to increase absorption of the gaseous carbon dioxide. While a shape of the particle 14 is not limited to a spherical, particulate shape as shown, a maximum dimension of the particle 14 (such as a diameter if the particle 14 is spherical or a major axis if the particle 14 is ellipsoidal) may range from about 100 µm to about 10,000 µm.

Various materials may be used for the binder particles 14, so long as the material used is capable of absorbing gaseous carbon dioxide, binding the same in a solid state, and does not adversely react with blood (such as facilitating clotting, for example). In some instances, the binder particles 14 may include at least one absorbent material selected from the group consisting of sodium oxide, sodium hydroxide, calcium oxide, calcium hydroxide, potassium hydroxide, lithium hydroxide, lithium peroxide, lithium carbonate, lithium chloride, and combinations thereof. For instance, in one embodiment, the binder particles 14 may include a combination of calcium hydroxide, sodium hydroxide, and potassium hydroxide. In another embodiment, the binder particles 14 may include a combination of lithium hydroxide and lithium carbonate. In still another embodiment, the binder particles 14 may include a combination of calcium hydroxide and lithium chloride.

According to some embodiments, the binder particles may comprise a first plurality having a first composition and a second plurality having a second composition.

Referring now to FIG. 2, a blood filtration cartridge 18 according to an embodiment of the present invention is shown and a housing 20, which may be formed from metal (such as stainless steel), a non-reactive material, or an inexpensive (and thus disposable) medical grade polymer material. The housing 20, as shown in the illustrated embodiment, may be cylindrical in shape with an overall length ranging from about 20 cm to about 30 cm and an outside diameter ranging from about 10 cm to about 15 cm. Proximal and distal end caps 22, 24 close the housing 20. A fluid tight seal may be accomplished by internal seals (such as O-rings, not shown), welding, epoxy, or other methods known to those of ordinary skill in the art.

A proximal inlet port 26 and a distal outlet port 28 provide fluidic communication with an internal cavity 30 (FIG. 3) of the housing 20. Each of the inlet and outlet ports 26, 28 may be configured to receive medical grade tubing, such as IV tubing (for example, constructed from silicone or PVC). As such, the ports 26, 28 may include a quick connect coupler, a barbed coupler, with or without flow valves, and other structures known by those of ordinary skill in the art.

Referring still to FIG. 2, with reference now also to FIG. 3, the internal cavity 30 of the housing 20 may include an embodiment of the absorption media 10, such as was illustrated in FIG. 1. The absorption media 10 is arranged such that lengthwise central axes 32 of the hollow fibers 12 generally aligns with a lengthwise central axis 34 of the housing 20. As such, as blood enters the housing 20 via the inlet port 26, blood may pass into the lumen 17 (FIG. 1) of the hollow fibers 12. Gaseous carbon dioxide in the blood may cross through the walls 16 of the hollow fibers 12 and be absorbed and bound to the binder particles 14. Remaining blood components (e.g., plasma, red blood cells, white blood cells, etc.) are maintained within the hollow fibers 12, pass through the length of the hollow fibers 12, and exit the internal cavity 30 via the distal port 28.

FIG. 4 illustrates a blood filtration cartridge 36 according to another embodiment of the present invention. The cartridge 36 includes a housing 38 with proximal and distal ports 40, 42; however, the internal cavity is split such that a first, proximate cavity 44 is fluidically sealed from the second, distal cavity 46. As such, proximal ends 17 of the hollow fibers 12 of the absorption media 10 extend proximally through a divider wall 48 and into the proximate cavity 44. In this embodiment, blood may only flow through the lumen of the hollow fibers 12 and may not enter the distal cavity 46 having the binder particles 14 therein.

Figure 5:
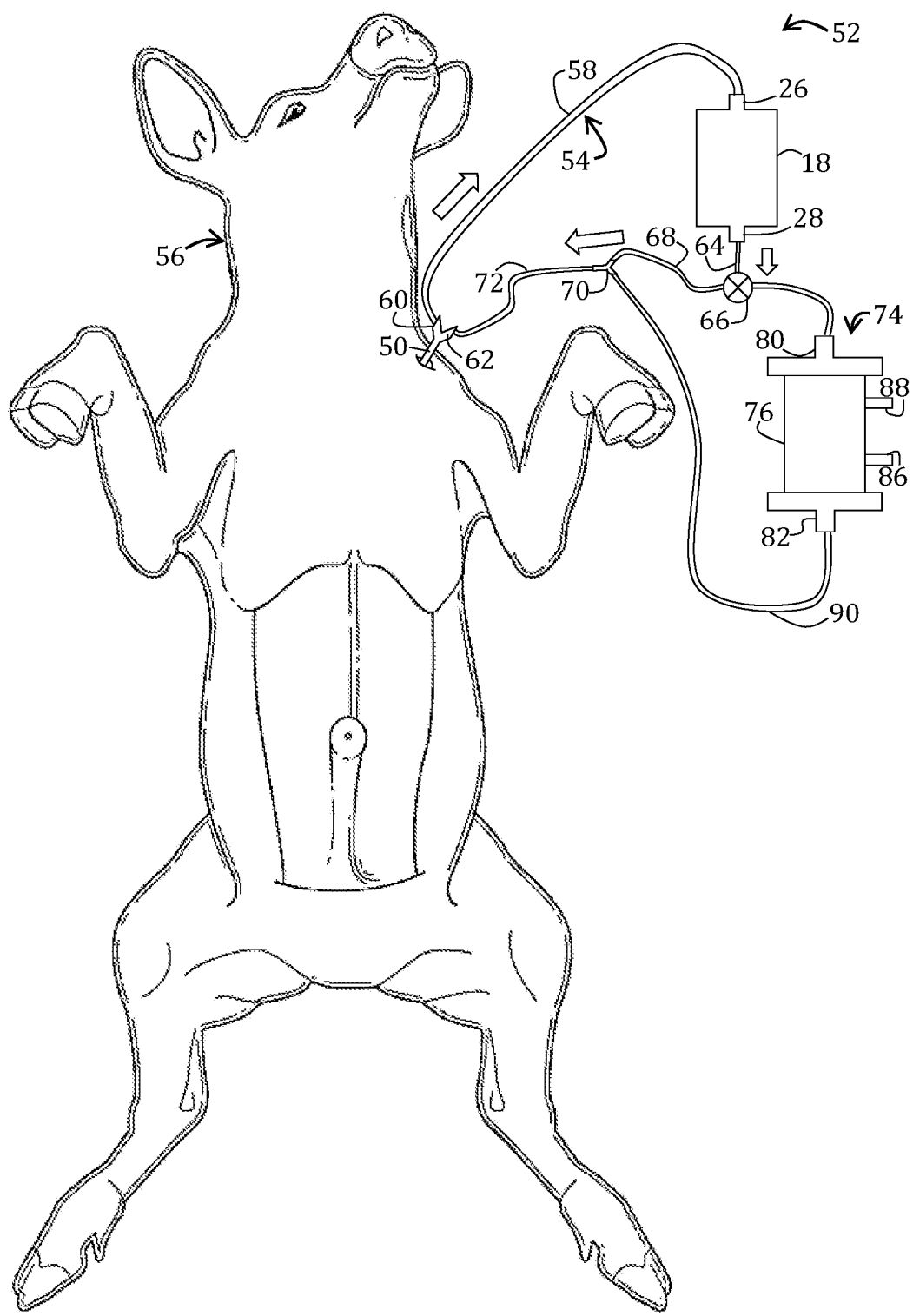
FIG. 5 is a schematic view of a system for extra-corporeal absorption of carbon dioxide from the blood of patient according to an embodiment of the present invention.

Blood filtration cartridges with an absorption medium according to embodiments of the present invention may be incorporated into an extra-corporal system, an example of which is shown in FIG. 5. In this illustrative embodiment, a dual lumen catheter 50 is inserted in a patient's vascular structure, for example, the jugular vein, the femoral vein, or others that are conventionally used for dialysis. In alternative embodiments, although not specifically illustrated here, an arteriovenous fistula or arteriovenous graft may be used. Regardless of the arteriovenous mechanism utilized, the extra-corporal system 52 includes a blood flow pathway 54 that extends from the patient 56 to the blood filtration cartridge 18 and returns to the patient 56. As such, a first tubing 58 (which may be any medical grade tubing, such as silicone or PVC) extends from an outflow port 60 of the dual lumen catheter 50 to the proximal inlet port 26 of the housing 20. As described previously, blood entering the proximal inlet port 26 flows through the absorption medium 10 (FIG. 1) such that gaseous carbon dioxide crosses over walls 16 (FIG. 1) of the hollow fibers 12 (FIG. 1) and is bound at the binder particles 14 (FIG. 1).

Blood exiting the blood filtration cartridge 18 may be returned to the patient 54 via the inlet port 62 of the dual lumen catheter 50. However, as specifically shown in FIG. 5, blood exiting the blood filtration cartridge 18 may optionally, by way of a second tubing 64 and valve 66, return to the patient 54 (via an illustrated third tubing 68, y-coupler 70, and fourth tubing 72 to the inlet port 62 of the dual lumen catheter 50), or may be diverted for further processing.

Figure 6:
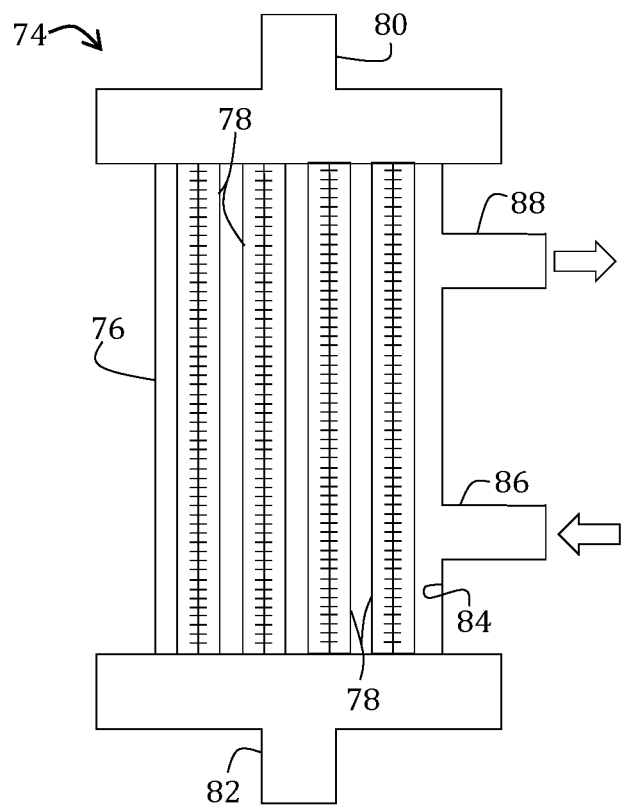
FIG. 6 is side elevational view of a dialyzer for use in accordance with the system illustrated in FIG. 5.

For example, blood flow may be diverted at the valve 66 to a dialyzer 74 for hemodialysis such that excess urea may also be removed from the blood. The dialyzer 74, which is illustrated with greater detail and in cross-section in FIG. 6, comprises a housing 76 packed with hollow fibers 78 that are selectively permeable to urea and other metabolic waste products but that are not permeable to blood components. Blood enters the housing 76 via a proximal port 80 and flows through hollow fibers 78 to the distal port 82. A dialysate (not shown) flows into a cavity 84 of the housing via a secondary inlet port 86. The dialysate does not cross over the selectively permeable hollow fibers 78 but, instead, creates a diffusion gradient that drives the metabolic waste products from the blood, across the hollow fibers 78 and into the dialysate. Dialysate, with metabolic waste, flows out of the housing 76 via a secondary outlet port 88 while blood returns to the blood flow pathway 54 via tubing 90. Dialysate flow through the housing 76 is arranged to be in a direction that is countercurrent to blood flow.

Although not specifically illustrated in FIG. 5, the system 52 may further include a pump configured to pump blood through along the blood flow pathway 54. This pump may be a peristaltic pump and tubing for the extra-corporeal blood flow pathway 54 may be is inserted into or attached thereto so that the pump moves the blood within the tubing without directly contacting the blood.

Flow rate of blood through the absorption media according to embodiments of the present invention may vary somewhat, depending for instance on the age, size, and condition of the patient being treated and dimension of the particular absorption media utilized in treatment. Typically, however, the blood flows through the absorption media at a rate from about 0.2 L/min to about 0.5 L/min.

The rate of carbon dioxide removal from the treated blood will also vary somewhat, depending for instance on the age, size, and condition of the patient being treated. Typically, however, the absorption media removes from about 50 mL/min to about 100 mL/min of carbon dioxide from the blood, measured at about atmospheric pressure and at a temperature from about 35° C. to about 39° C.

Importantly, and advantageously, because the carbon dioxide is absorbed and retained by the binder particles of absorption media according to embodiments of the present invention, the carbon dioxide may be removed without the need for a continuous flow of a carrier gas. Optimally, there is no carrier gas present at all. Thus, bulky high-pressure gas cylinders and associated hardware (pressure regulation gauges and other safety equipment) are not needed—leading to an extra-corporeal carbon dioxide removal system which is smaller in size and simpler in use. Moreover, the extracorporeal carbon dioxide removal system according embodiments of the present invention is well suited to use in austere treatment environments and/or in treatment environments with limited physical space, such as in aeromedical evacuations.

In some instances, the carbon dioxide absorption system may include or work in conjunction or parallel to a dialyzer. Thus, in such a system, hemodialysis may be performed on the blood to remove excess urea from the blood at the same time as the carbon dioxide removal.

Embodiments of the present invention also provide a method for treating a patient suffering from excessively high carbon dioxide levels in the blood (i.e., hypercapnia). In accordance with this method, blood having an elevated amount of carbon dioxide is withdrawn from a first vascular structure of a patient and directed to a cartridge having a carbon dioxide absorption medium according to an embodiment of the present invention disposed therein. As the blood flows through the cartridge, gaseous carbon dioxide from the blood passes across the semi-permeable walls of hollow fibers 12 and is absorbed by and bound to binder particles 14, effectively reducing an amount of carbon dioxide in the blood. After passing through the cartridge, the blood is returned to the patient via a second vascular structure.

As noted above, in some instances, the treatment method of the present disclosure may also include a step of performing hemodialysis on the blood using a dialyzer to remove excess urea from the blood.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:
1. A carbon dioxide absorption medium comprising:
a plurality of hollow fibers, each hollow fiber of the plurality having a proximal end, a distal end, a lumen extending between the proximal and distal ends, and a wall surrounding the lumen, the wall of each hollow fiber of the plurality comprising a membrane selectively permeable to gaseous carbon dioxide; and
a plurality of binder particles dispersed between hollow fibers of the plurality, each binder particle of the plurality being configured to absorb gaseous carbon dioxide and to bind and to retain the carbon dioxide in a solid state.
2. The carbon dioxide absorption medium of claim 1, wherein the membrane comprising the wall of each hollow fiber of the plurality comprises at least one polymer selected from the group consisting of cellulose acetate, cellulose triacetate, polyamide, polysulfone, polyethersulfone (PES), polyacrylonitrile (PAN), sulfonated polyacrylonitrile, polymethylmethacrylate (PmmA), and polymethylpentene (PMP).
3. The carbon dioxide absorption medium of claim 1, wherein the wall of each hollow fiber of the plurality has an outer thickness ranging from about 5 μm to about 50 μm.
4. The carbon dioxide absorption medium of claim 1, wherein the binder particles of the plurality have a maximum dimension ranging from about 100 μm to about 10,000 μm.
5. The carbon dioxide absorption medium of claim 1, wherein the plurality of binder particles comprise at least one absorbent material selected from the group consisting of sodium oxide, sodium hydroxide, calcium oxide, calcium hydroxide, potassium hydroxide, lithium hydroxide, lithium peroxide, lithium carbonate, and lithium chloride.
6. A carbon dioxide absorption cartridge for removing carbon dioxide from the blood of a patient, the cartridge comprising:
a housing having an inlet port and an outlet port and an internal cavity therebetween, the inlet port configured to fluidically receive blood from the patient and the outlet port configured to fluidically return filtered blood to the patient; and
the carbon dioxide absorption medium of claim 1 disposed within the internal cavity of the housing.
7. The cartridge of claim 6, wherein the membrane comprising the wall of each hollow fiber of the plurality comprises at least one polymer selected from the group consisting of cellulose acetate, cellulose triacetate, polyamide, polysulfone, polyethersulfone (PES), polyacrylonitrile (PAN), sulfonated polyacrylonitrile, polymethylmethacrylate (PmmA), and polymethylpentene (PMP).
8. The cartridge of claim 6, wherein the wall of each hollow fiber of the plurality has an outer thickness ranging from about 5 μm to about 50 μm.
9. The cartridge of claim 6, wherein the binder particles of the plurality have a maximum dimension ranging from about 100 μm to about 10,000 μm.
10. The cartridge of claim 6, wherein the plurality of binder particles comprise at least one absorbent material selected from the group consisting of sodium oxide, sodium hydroxide, calcium oxide, calcium hydroxide, potassium hydroxide, lithium hydroxide, lithium peroxide, lithium carbonate, and lithium chloride.
11. The cartridge of claim 6, wherein the internal cavity of the housing comprising a first partition and a second partition fluidically isolated from the first partition, wherein the proximal ends of the hollow fibers of the plurality extend into the first partition while the distal ends of the hollow fibers of the plurality and the plurality of binder particles reside within the second partition such that flow of blood through the housing is restricted to flow through the plurality of hollow fibers.
12. The cartridge of claim 6, wherein the absorption medium removes carbon dioxide from the blood at a rate ranging from about 50 mL/min to about 100 mL/min as measured at about atmospheric pressure and at a temperature from about 35° C. to about 39° C.
13. The cartridge of claim 6, wherein the blood flows through the absorption medium at a rates ranging from about 0.2 L/min to about 0.5 L/min.
14. A blood treatment system comprising:
the carbon dioxide absorption cartridge of claim 6;
a first blood flow pathway extending between a patient and the inlet port of the housing of the carbon dioxide absorption cartridge; and
a second blood flow pathway extending between the outlet port of the housing of the carbon dioxide absorption cartridge and the patient.
15. The blood treatment system of claim 14, further comprising:

a pump configured to pump blood between the patient and the carbon dioxide absorption cartridge along the first and second blood flow pathways.

16. The blood treatment system of claim 14, further comprising:
a dialyzer along the first blood flow pathway or the second blood flow pathway and configured to perform hemodialysis.

17. A method for removing carbon dioxide from blood, the method comprising:
transporting blood from a patient to a carbon dioxide absorption cartridge, the carbon dioxide absorption cartridge comprising:
a housing having an internal cavity therein; and
a carbon dioxide absorption medium disposed within the internal cavity of the housing, the carbon dioxide absorption medium comprising a plurality of hollow fibers, each hollow fiber of the plurality having a proximal end, a distal end, a lumen extending between the proximal and distal ends, and a wall surrounding the lumen, the wall of each hollow fiber of the plurality comprising a membrane selectively permeable to gaseous carbon dioxide and a plurality of binder particles dispersed between hollow fibers of the plurality, each binder particle of the plurality being configured to absorb gaseous carbon dioxide and bind the carbon dioxide in a solid state;
moving the blood through the carbon dioxide absorption cartridge, thereby removing carbon dioxide from the blood; and
transporting the blood from the carbon dioxide absorption cartridge to the patient,
wherein neither a carrier fluid flow nor a sweep fluid flow is required for removing carbon dioxide from the blood of the patient.

18. The method of claim 17, wherein the membrane comprising the wall of each hollow fiber of the plurality comprises at least one polymer selected from the group consisting of cellulose acetate, cellulose triacetate, polyamide, polysulfone, polyethersulfone (PES), polyacrylonitrile (PAN), sulfonated polyacrylonitrile, polymethylmethacrylate (PmmA), and polymethylpentene (PMP).

19. The method of claim 17, wherein the wall of each hollow fiber of the plurality has an outer thickness ranging from about 5 µm to about 50 µm and the binder particles of the plurality have a maximum dimension ranging from about 100 µm to about 10,000 µm.

20. The method of claim 17, wherein the plurality of binder particles comprise at least one absorbent material selected from the group consisting of sodium oxide, sodium hydroxide, calcium oxide, calcium hydroxide, potassium hydroxide, lithium hydroxide, lithium peroxide, lithium carbonate, and lithium chloride.

21. The method of claim 17, wherein carbon dioxide is removed from the blood at a rate ranging from about 50 mL/min to about 100 mL/min.

22. The method of claim 17, wherein blood flows through carbon dioxide absorption cartridge at a range ranging from about 0.2 L/min to about 0.5 L/min.

23. The cartridge of claim 6, wherein neither a carrier fluid flow nor a sweep fluid flow is required for removing carbon dioxide from the blood of the patient.

* * * * *